United States Patent [19]
Kenyon

[11] Patent Number: 5,441,501
[45] Date of Patent: Aug. 15, 1995

[54] INTERMEDULLARY RASP WITH DETACHABLE EXTENSION END

[75] Inventor: Roger R. Kenyon, Fort Wayne, Ind.

[73] Assignee: Zimmer, Inc., Warsaw, Ind.

[21] Appl. No.: 263,361

[22] Filed: Jun. 20, 1994

[51] Int. Cl.⁶ ............................................. A61B 17/00
[52] U.S. Cl. ...................................................... 606/85
[58] Field of Search ........................ 606/85, 79, 80, 84; 623/23; 29/78, 79, 80

[56] References Cited

U.S. PATENT DOCUMENTS

| | | | |
|---|---|---|---|
| 2,547,484 | 4/1951 | Murdach et al. | 29/80 |
| 4,888,023 | 12/1989 | Averill et al. | 623/22 |
| 5,030,234 | 7/1991 | Pappas et al. | 623/23 |
| 5,057,101 | 10/1991 | Dorr et al. | 623/23 |
| 5,074,879 | 12/1991 | Pappas et al. | 623/18 |
| 5,089,004 | 2/1992 | Averill et al. | 623/23 |
| 5,108,452 | 4/1992 | Fallin | 623/23 |
| 5,147,408 | 9/1992 | Noble et al. | 623/23 |

FOREIGN PATENT DOCUMENTS

| | | | |
|---|---|---|---|
| 161094 | 10/1957 | Sweden | 29/78 |
| 246513 | 10/1947 | Switzerland | 29/78 |

OTHER PUBLICATIONS

Osteonics, (Product Reference Hip C-7, C-12).
Intermedics—Advanced Instrumentation Brochure, pp. 30-31.

*Primary Examiner*—Tamara L. Graysay
*Attorney, Agent, or Firm*—Todd A. Dawson

[57] ABSTRACT

A rasp-like instrument for forming a cavity in the intermedullary passage of a femur for the implantation of a femoral stem prosthesis. The rasp includes a detachable extension end which can be removed when the rasp is used to form the cavity for the primary implant stem and connected to provide a deeper cavity for the revision implant stem.

3 Claims, 2 Drawing Sheets

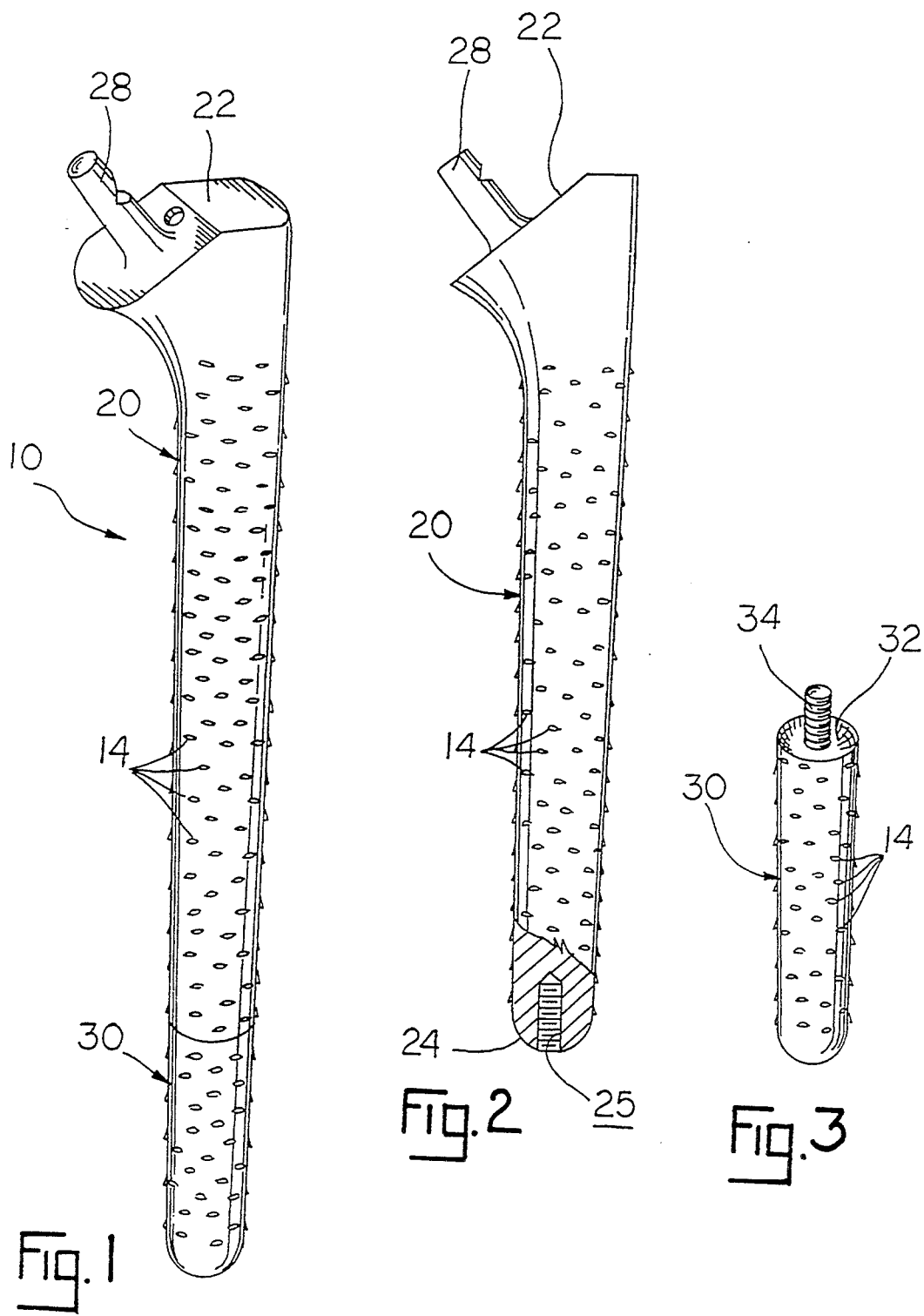

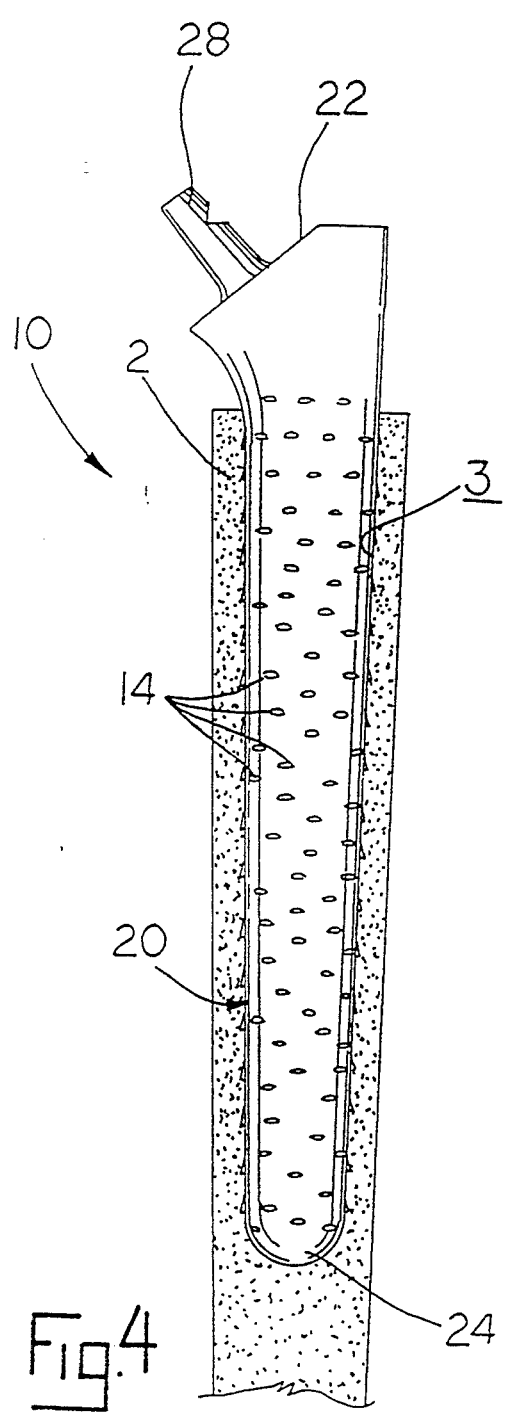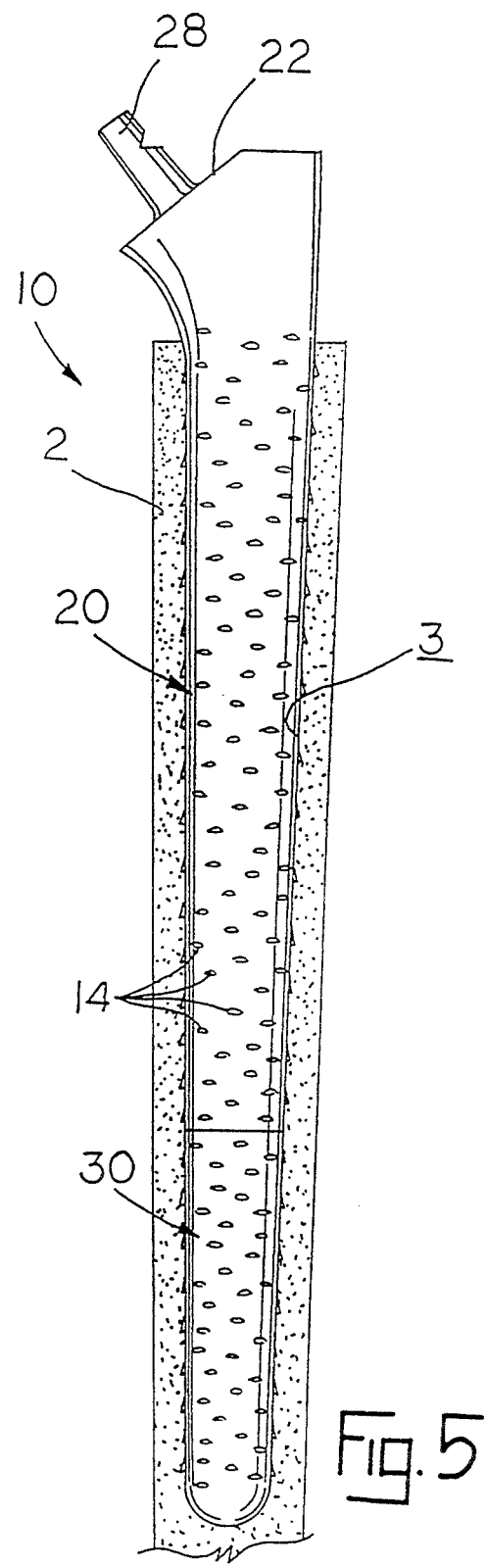

INTERMEDULLARY RASP WITH DETACHABLE EXTENSION END

This invention relates to a rasp-like instrument for forming a cavity in a bone and particularly a femoral rasp and a detachable extension end for preparing a cavity in the intermedullary passage of a femur for the implantation of a femoral stem prosthesis.

BACKGROUND OF THE INVENTION

The use of prosthetic implants to replace natural joints of the body is well known. In a hip joint replacement, a femoral head is replaced by a prosthetic head connected to a prosthetic femoral stem. The implant stem is fitted into a cavity formed in the intermedullary passage of the femur. Generally in the surgical procedure, a rasp-like instrument is driven into the intermedullary passage to prepare the cavity for receiving the implant stem. The rasps are generally contoured to gross geometry of the implant stem to assure an accurate location and precise fit. Revisional implant stems are typically longer than the primary to provide secure foundations within the bone. Consequently, the rasp which forms the receiving cavity for the revision implant stem must also be longer than the rasp used in the primary procedures. Including additional rasps with varied lengths adds to the instrument count and costs to the hospital and manufacturer.

SUMMARY OF THE INVENTION

The rasp of this invention eliminates the need for multiple rasps of various lengths to accommodate both the implantation of a primary implant and any subsequent revision. The rasp includes a detachable extension end which can be removed when the rasp is used to form the cavity for the primary implant stem and connected to provide a deeper cavity for the revision implant stem. Using a single rasp with a detachable extension end reduces the instrument count in the procedure thereby reducing costs to the hospital and manufacturer.

Accordingly, an object of this invention is to provide for a novel and unique rasp-like reaming instrument for use in the preparation for implantation of a femoral implant stem prosthesis.

Another object of this invention is to provide for an orthopedic rasp which can be used in the implantation procedures for both the primary implant and a revision implant.

Another object of this invention is to provide for a rasp with a detachable extension end.

Other objects will become apparent upon a reading of the following description.

BRIEF DESCRIPTION OF THE DRAWINGS

A preferred embodiment of the invention has been depicted for illustrative purposes only wherein:

FIG. 1 is a perspective view of the rasp of this invention showing the extension end connected to the rasp body.

FIG. 2 is an exploded view of the rasp body.

FIG. 3 is a perspective view of the extension end.

FIG. 4 is a sectional view of the rasp body driven inside a medullary passage of a bone to form a cavity.

FIG. 5 is a sectional view of the rasp body and connected extension end driven inside the medullary passage of a bone to form an extended cavity.

DESCRIPTION OF THE PREFERRED EMBODIMENT

The preferred embodiment herein described is not intended to be exhaustive or to limit the invention to the precise form disclosed. It is chosen and described to explain the principles of the invention and its application and practical use to enable others skilled in the art to utilize its teachings.

FIGS. 1–3 show the rasp 10 of this invention. Rasp 10 includes an elongated tapered body 20 and detachable extension end 30. Rasp body 20 is substantially shaped to conform to the outer space of the implant stem which will be used. As shown in the figures, rasp body 20 has a proximal end 22 and a distal end 24. A mounting post 28 extends from proximal end 22. Mounting post 28 and indexed locating hole 29, which is of conventional design and well known in the art, is used to connect rasp 10 to a rasp handle (not shown) for driving the rasp into the bone. The mounting post and indexed locating hole also allow the rasp to be fitted with various provisionals and implant heads to determine the appropriate size and test the initial positioning of the implant stem. A threaded axial bore 25 is formed in the tip of distal end 24. Extension end 30 has an elongated configuration conforming substantially to the taper of rasp body 20. Extension end 30 has a concave connecting face 32 which mates with the convex face of distal end 24. A threaded post 34 extends axially from face 32 of extension end 30, which is threaded to mate with bore 25 in rasp body 20. As shown in the figures, both rasp body 20 and extension end 30 have a plurality of cutting teeth 14. Teeth 14 or similar structures commonly found in the art are used to shave portions of the bone tissue to form the implant cavity as the rasp is driven into the intermedullary passage of the femur.

FIG. 4 shows the rasp used to form a cavity 3 in a femur 2 for a primary implant stem (not shown). FIG. 5 shows rasp 10 used to form a lengthened cavity 3 for a revision implant stem (not shown). When the rasp is used in a revision implantation procedure, the extension end 30 is connected to rasp body 20. Post 34 of extension end 30 is turned into bore 25 of rasp body 20. The additional length provided by extension end 30 provides a deeper cavity to accommodate the additional length of the revision implant stem.

While the preceding exemplary embodiments have focused on a rasping instrument used in a femoral implantation procedure, it will be understood that the apparatus and techniques described are applicable to other types of implantation procedures, the rasp instrument geometry being adjusted accordingly. It should be understood that the shape of the rasp shown is merely illustrative. In practice, the rasp would be shaped to substantially conform to the shape of the implant. Finally, it is understood that the above description does not limit the invention to the details given, but may be modified within the scope of the following claims.

I claim:

1. An apparatus for preparing a first cavity in a bone in preparation for an initial implant prosthesis and for preparing an extended second cavity in said bone in preparation for a revision implant prosthesis, wherein the second cavity is longer than the first cavity, said apparatus comprising:

an elongated body part adapted to conform to the shape of a prosthesis to be implanted in said bone, said body part having a proximal end and a distal end, and an elongated extension part for connection to the distal end of the body part to lengthen the body part, means for longitudinally connecting said extension part to said body part for forming the second cavity, teeth means carried by said body part and said extension part for cutting a portion of said bone to produce said second cavity, said extension part connected to said body part by said connecting means when said apparatus is used for preparing said second cavity.

2. The apparatus of claim 1 wherein said connecting means includes a longitudinal end bore defined in said body part distal end and a post extending longitudinally from said extension part, said end bore being adapted for restrictively receiving said post therein.

3. A femoral rasp for forming an interior envelope within a proximal femur, the rasp including a proximal end and a distal end defining a first length, a plurality of teeth being formed along at least a portion of the rasp, the rasp further including an extension part having a proximal end and a distal end for connection to the distal end of the rasp at the proximal end of the extension part, the extension part having a plurality of teeth thereon, wherein the rasp with extension part connected thereto defines a second length, wherein the first length is shorter than the second length.

* * * * *